United States Patent [19]

Daneshvar

[11] Patent Number: 5,792,061
[45] Date of Patent: Aug. 11, 1998

[54] DUAL POWERED PRESSURE INFLATOR AND METHOD

[76] Inventor: Yousef Daneshvar, 21459 Woodfarm, Northville, Mich. 48167

[21] Appl. No.: 434,840

[22] Filed: May 4, 1995

[51] Int. Cl.$^6$ ................................................. A61B 5/02
[52] U.S. Cl. ........................ 600/499; 600/490; 600/493
[58] Field of Search ........................ 128/672, 677–686; 92/92; 606/202

[56] References Cited

U.S. PATENT DOCUMENTS

| | | | |
|---|---|---|---|
| 4,691,710 | 9/1987 | Dickens et al. | 128/672 X |
| 5,201,319 | 4/1993 | Negishi | 128/686 X |
| 5,540,231 | 7/1996 | Moy | 128/680 X |

Primary Examiner—Robert L. Nasser
Assistant Examiner—Ryan Carter

[57] ABSTRACT

This invention considers the problem with inflation of the units by hands, and introduces a dual action inflation unit to be used for measurement of the blood pressure cuff and similar units such as D. Devices. The prototype of this unit consists of an electrical/pedal pumps combined with a manual inflation units. This will allow the electrical/pedal pumps to be used first for inflation of most of the inflatable part and then the manual unit will be used for a lesser degree of inflation as well as the adjustment of the inflation units. This combination is to prevent straining of the hands. It will also allow quick and easy action. This unit also allows a trigger system to be used for controlling the pressure in the system to prevent from the discomfort of the rotational action; it also has safety valves to prevent the pressure from exceeding a predicted level.

17 Claims, 2 Drawing Sheets

DUAL POWERED PRESSURE INFLATOR AND METHOD

BACKGROUND OF THIS INVENTION

The inflation of the balloon of the applicant's unit D. Device and the blood pressure cuffs are presently done by a manual bulb made from rubber and is basically a hand operated unit. This unit is to be squeezed by hands to pump the air against pressure, which is not an easy job, especially if it has to pump many times or if the user has arthritis, hand problems or similar conditions. Therefore, the applicant introduces an inflator system that has a dual power for the inflation and allows an easier inflation of such units. These units also avoids the use of rotational methods for operation of the valves which is hard for some people with hand problems.

BRIEF EXPLANATION OF THE INVENTION

This application introduces a method and a system of inflation of pressure operated balloons and pressure cuffs in which an electrical/pedal pumps will be used with the manual inflation units together. These systems and method will allow a pedal or an electric inflation unit to be used for most of the inflation. The minor inflation for the adjustment of the pressure will be done with the use of a manual unit. However, the manual unit may be of any kind such as the hand-held rubber bulbs. The system and method will have a means of control such as an air release part to allow for the adjustment of pressure. This system and method will eliminate the need for pumping the cuff only by hand. This unit may be made to stand on the walls or may have a stand with wheels to allow it to be moved around easily. The unit will also use a gauge to measure the pressure and it may also have safety valves to prevent the pressure from exceeding a predicted level.

DETAILED EXPLANATIONS OF THE FIGURES

Figure 1:
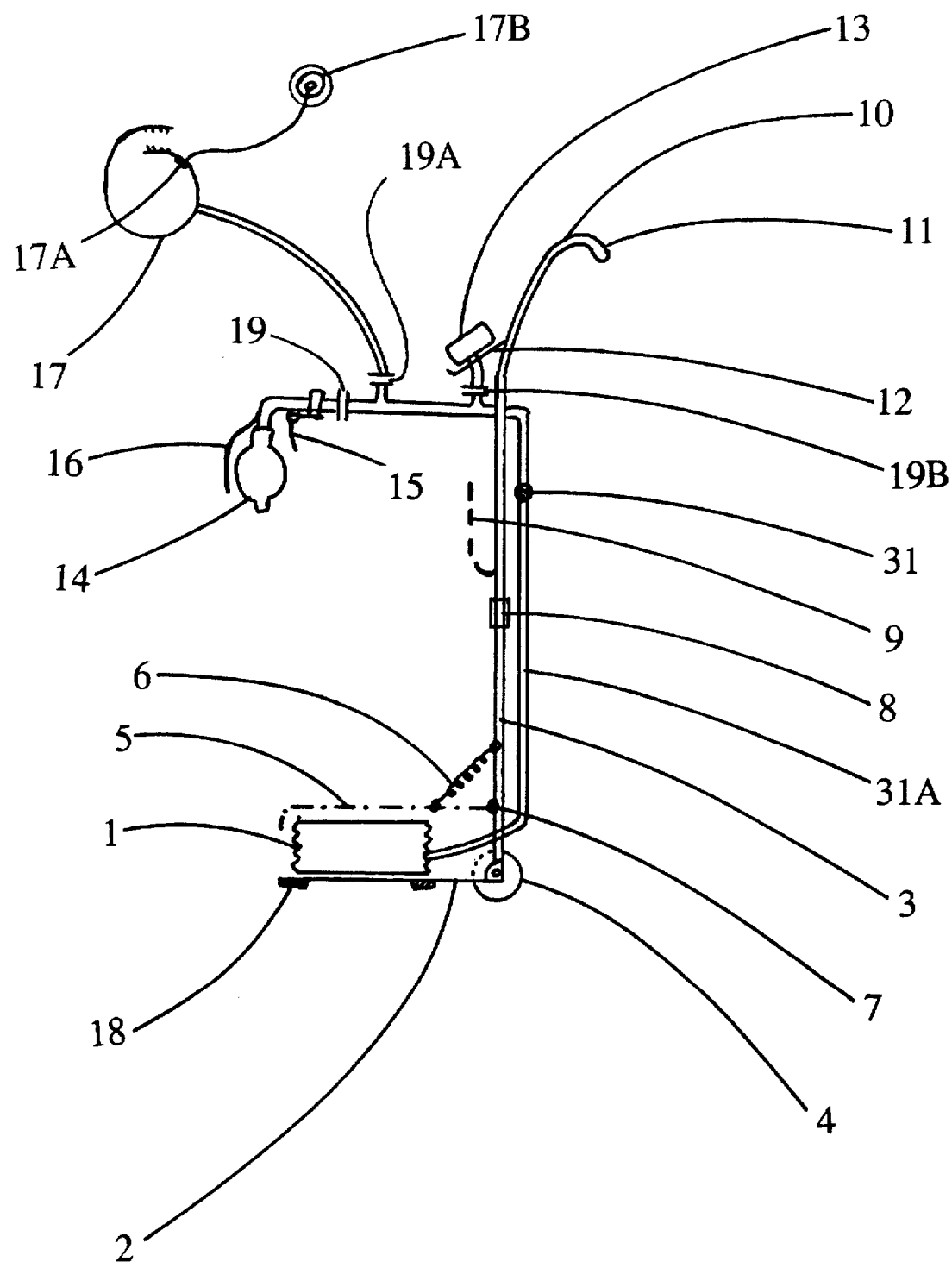
FIG. 1. Shows general composition of such as unit.

FIG. 1. This fig schematically shows a unit that has a source of inflation such as 1. This source can be a pedal operated unit, an electrical pump that will produce a pressurized air for inflation or even a compressed air cylinder. In this model the inflator 1 is mounted on a portable unit consisting of a lower flat piece 2 that will stand on the floor and allows the foot to compress the inflator 1. This piece may have patches in its bottom such as the one shown at 18 to level the surface and also to give a better grip to the unit and the floor. These may be made from rubber or similar materials. The base 2 has an adjustable handle 3 that will allow this unit to be moved around the wheels 4 (one on each side of the base will allow the unit to be wheeled away in the rooms or halls. The flat pedal piece 5 is to allow the person to use his/her foot for compression of the inflator means 1. This piece is hinged to the body of the unit at 7. The spring 6 is connected between the flat pedal piece 5; the body 3 from the unit will return the flat pedal piece 5 up after being pressed down. The adjustable means 8 will allow the height of this unit to be adjusted. The basket 9 will hold the bulb 14 and cuff 17 and similar ancillary pieces. The handle 10 will allow the unit to be wheeled around easily and the piece 11 will allow the unit to be hanged on the sides of the tables, stretchers, etc. The bracket 12 schematically shows a part that will hold the manometers means in place securely. No.13 is to show the means of measuring the pressure which can be of any kind. Importantly, this part may have an adjustable control valves/means in order to allow the maximum level of the pressure to be set prior to its use so that the pressure will not exceed that level. The hand-held inflator bulb 14 has the control means of 15 to allow the air flow to be controlled. This can be of any kind. Here the applicant suggests it to be from a kind that will use a trigger type action in order to be handled easily and avoid the rotational movements. The support wall 16 will allow the bulb 14 to be compressed against it. No.17 shows the cuff means as the unit that needs to be inflated. Importantly, this cuff may also have an electrical powered sensor 17A that will peak up the sound waves created by the motion of the blood inside a partially occluded artery by pressure and it will relay those sounds to the speaker 17B or a similar unit that may be functional alone or may be connected to a stethoscope to be heard. The sensor unit also may be connected to a computer to affect the function of the electrical pump. For example, in order to shut it off after the noises of the artery stop due to pressure. The unit may also have a three-way stopcock 19A in the beginning of the tubing for the pressure cuff in order to allow the unit to be selectively connected to another unit such as a manually powered pressurizing device or D. Device (this is a balloon placed under a wrap on the wound of the groin after cardiac catheterization for prevention of bleeding in that area, and the inflation of the balloon is rather difficult if done by hands) in order to allow not only the D. Device to be inflated and used, but also the blood pressure of the patient to be checked at that time by this system very conveniently.

Please notice that many of the connection spots as shown by two small parallel lines at 19, 19B are detachable in order to allow different units to be connected to these units.

These connection areas may have means of securing them to each other.

Figure 2:
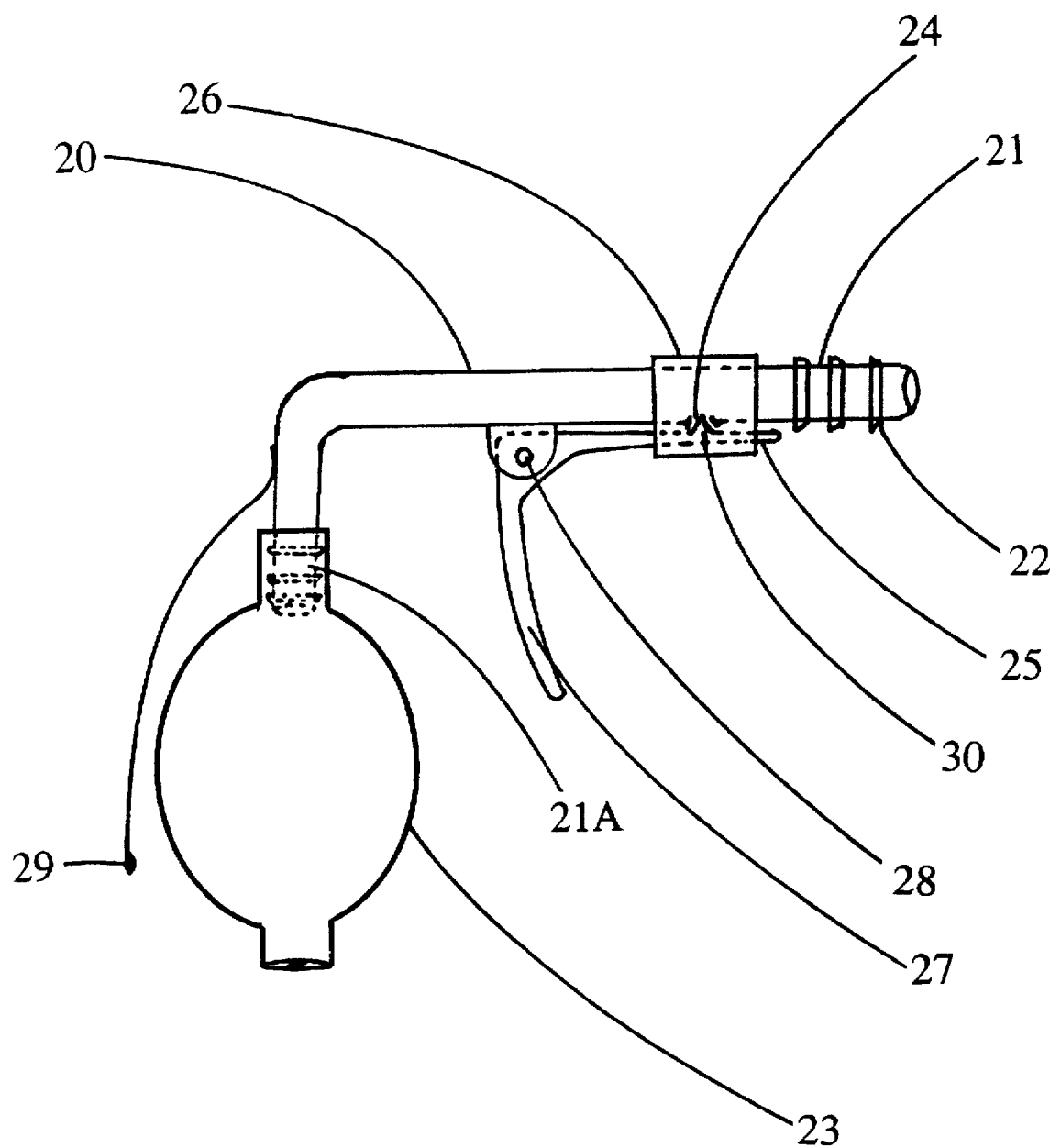
FIG. 2. Shows a larger view of the hand-held pump unit 14 FIG. 1

FIG. 2. This fig is to schematically show a larger view of the hand-held pump unit 14 FIG. 1 which is designed to be a trigger means for the control of the air release. Also, the unit allows an easy inflation as well due to its special design. In this fig the body of the tubing 20 is shown that has an angled body with one end 21 to be connected to the incoming tubing and another end 21A that will allow it to be connected to the body of an inflation bulb 23. The end pieces of this tubing has the raised short walls 22 in order to allow a secure connection of this piece and the other pieces to occur. This tubing has a small opening 24 which will allow the air or fluid to leave the system. This opening will be covered and closed by a matching piece 30 from the control 25 which will be held in place by a properly sized elastic band 26 so that the band will hold the closing part of the piece 25 firmly against the hole 24 and will prevent from air leakage. The piece 25 has a trigger shaped handle 27 that is hinged by the means 28 to the body of the tubing 20 so that when the trigger is pressed the air will leak out and this will be a controlled means to allow the amount of air leakage to be decided. The bulb 23 has a matching flat, rigid, guard piece 29 which is designed to allow the bulb to be pressed against it for a better squeeze. No.31 shows a one way valve in the tube 31A that will allow the air to move forward but not return into the pump. This valve may be placed any place in the system (inside the pump or in the tubing).

DETAILED EXPLANATION OF THIS INVENTION

The inflation of the balloons of the applicant's unit D. Device and the blood pressure cuffs and similar units are presently done by a manual bulb made from rubber. This is a hand-held unit and is to be squeezed by hands to pump the air against pressure inside the balloon of the D. Device or the body of the blood pressure cuff and similar units. However, this is not an easy job especially if the user has to pump many times or if he/she has arthritis, hand problems or a condition that makes the frequent use of the hand and fingers uncomfortable and painful. This new unit will minimize this problem to a great degree. In these models a pedal or an electrical air compressor will be used to generate most of the pressurized air and to inflate the unit to an optimal level. Then a hand operated unit such as commonly used rubber bulbs will be used to adjust the inflation to a minute degree: small adjustments can be made if the user desires so that the use of the hands will be decreased significantly. Furthermore, the hand-held unit has a mean of control of the flow of the air as well so that it will block the movement of the air: to stop or to release it. Further improvements are also designed to make this unit a convenient unit to be used for measurements of blood pressure or to be used with units such as D. Devices. The advanced mini computers will also allow useful programming to be made. For example: the use of a mini computer will allow functioning of the electrical pump to be controlled; in routine measurements of the blood pressure it will allow the pump to work until the systolic or the upper pressure of the patient is reached and slightly exceeded. Then the computer will shut off the pump and allow the hand-held unit to be used for adjusting the pressure and for the continuation of the process. The computer will also allow certain functions to be used for control of devices such as D. Device. In such a case the computer will allow the unit to be inflated, holding the pressure for a certain period of time and then it will allow a lower pressure to be applied and the course to continue. Importantly, this computer will also allow an alarm to be used if the pressure of the system drops unexpectedly or if there is a need for sudden inflation of the unit to a higher pressure. For instance in the case of bleeding this will make a very useful unit. The hand-held unit will allow the unit's pressure to be adjusted any time that is required as it does occur with the use of D. Devices.

This computer part may be placed in the gauge area as shown at 13 FIG. 1. The computer may also be useful in mechanical cases as well to allow the alarm unit to be functional, etc.

The basic units and other important pieces will be as follows:

1. The system will have an means of inflation (here referred as the second inflation means) schematically shown at no.1 FIG. 1 that allows an easy and quick inflation of the needed units to be done. This means of inflation can be of any kind such as a pedal-operated unit that allows the feet to pump the air into the system, an electrical pump that will use electricity, a battery, even a unit of compressed air cylinder, or any other similar means. This part is to make the initial inflation and most of the inflation to be easy, quick and without the need to use the hand for compression. Such a unit may be placed in any proper site of this system or it may be placed on a stand that can be moved easily by holding its hands or the use of the wheels. This unit may be chosen to be a pedal inflator made from a cylinder and piston, a proper inflation bulb, or similar means, etc. The pedal inflator will be mounted on a portable stand and a prototype of such unit is shown in FIG. 1. This unit will consists from a lower flat piece 2 that will be placed on the floor of the room and allows the foot to compress the inflator 1. The bottom surface of the lower flat pedal piece may have patches of rubber in its bottom such as the one shown at 18 to level the surface and also to give a better grip between the unit and the floor. The base 2 will have an adjustable pole or a handle 3 that will allow this unit to be moved around easily. The unit also may have a series of wheels 4. to allow the unit to be wheeled away easily when desired. The system may have a pedal or a flat pedal piece 5 in order to allow the user to compress the inflator 1 by his/her foot. The upper surface of this piece may also have a patch of rubber or similar material to prevent skidding. The pedal may be connected to the body of the unit by various means. in this prototype model it is hinged to the pole of the unit at 7 and the spring mean 6 connected between the flat pedal piece 5 and the pole 3 of the unit will cause the piece 5 to return to its original position after being pressed. The height of the pole 3 can be adjusted with the use of means 8 which can be of any available kinds. The basket 9 is to hold certain units such as a hand-held inflation bulb 14. the cuff 17, and similar ancillary pieces inside. The handle 10 will allow the unit to be wheeled around easily and the hanger 11 will allow the unit to be hanged on the sides of the tables, stretchers, etc. The bracket 12 is to schematically show a part that will hold the gauge means or the manometers in place securely.

Please notice that in some models this unit may be stationary or in cases such as electrical units it may be placed on the wall to be functional.

2. The unit will also have a hand-held inflator unit (here referred to as the first inflator means) which will be used primarily for a small degree of inflation and adjustments as well. This inflator means can be of any form such as a small pump and in the prototype model it will be an inflator bulb such as the one shown at 14. The construction of the position of this bulb may be designed differently to allow a rather easier way of holding it, in order to make it held in the hand like the body of a pistol; this is to make it easier to be used. One sample of this unit is shown in more details in FIG. 2. This unit is designed to allow a trigger means to be used for the control of the air release. Also, the applicant believes that it will allow an easy inflation as well due to its special design. In FIG. 2 the tubing 20 has an angled body with one front end 21 to be connected to the incoming tubing and another rear end 21A that will accept the inflation bulb 23. The end pieces of this tubing has raised short walls 22 in order to allow a secure connection of this piece and the tubings or other pieces to occur. This tubing has a small opening 24 which will allow the air or fluid to leave the system. This opening will be covered and closed by a matching piece 30 from the control 25 which will be held in place by a properly sized elastic band 26 so that the band will hold the closing part 30 of the piece 25 firmly against the hole 24 and will prevent air leakage. A piece of rubber may help prevent air leakage or other methods may be used for this purpose. The piece 25 has a trigger shaped handle 27 that is hinged to the body of tubing 20 at hinge mean 28 so that by pressing the trigger 27 the air will leak in a controlled fashion. The bulb 23 may have a matching flat, rigid, guard 29 which is designed to allow the bulb to be pressed against it for a better squeeze. No.31 shows a one way valve that will allow the air to move forward but not to return into the pump. This valve may be placed any place in the system (inside the pump or in a segment of the tubing after connection of two pumps).

3. This system will use a means for measuring pressure inside the unit. This is symbolically shown at No.13. This unit can be of any possible kind such as spring operated units, mercury operated units, digital or computer operated units or any other measuring devices that may be used for the purpose of measuring the pressure in these units.

4. The control means 15 of these units can be of any kind such as the use of the conventional rotational valve, but it may use other means and methods of releasing air from the system. Here, the use of a trigger type action is advised in order to allow it to be handled easily and avoid rotational movements. This system was schematically introduced in this applicant's previous applications. The control part may also have an electrical switch in order to allow the electrical pump to be operated and controlled.

5. The unit may also have an adjustable control safety valves/means in order to allow the maximum level of the pressure to be set prior to inflation so that the pressure will not exceed that level. This is to prevent from accidental problems due to over-inflation. The unit may release air if this level is exceeded, and it may also shut off electric pumps if they are used for inflation.

6. Importantly, the second inflation unit of this system may be made from different means such as an expandable bulb made from a rubber type material with a cylinder shape and an accordion type wall (or in any other shape) in order to expand after compression. This part may also have a spring means in order to facilitate the expansion or to make the expansion faster. This inflation unit may consist from other inflation means such as a piston and cylinder or it may be a battery or electricity operated pump.

7. The cuff for measuring blood pressure may also have an electrically powered adjustable sensor symbolically shown in FIG. 1 at 17A that will sense the noise created by the motion of the blood inside a partially occluded artery by pressure and will relay those sounds to an adjustable speaker or similar unit (here symbolically shown at 17B) that will allow the examiner to hear it. This will let the examiner stop the inflation by the second unit when the systolic pressure of the patient is exceeded. This cuff may also have a connected stethoscope to allow the unit to be compact. The sensor unit may also be connected to a mini computer to affect the functioning of the electrical pump: for example, in order to shut it off after the artery's noise stops due to pressure.

8. The unit may also have a three-way stopcock 19A in the beginning of the tubing for the pressure cuff in order to allow the unit to be connected to another unit such as D. Device in order to allow not only the D. Device to be inflated and used but also the blood pressure of the patient to be checked at that time by this system very conveniently. Please notice that many of the connection spots as shown at 19, 19B in FIG. 1 by two small parallel lines are detachable in order to allow different units to be connected to these units. These connection areas may have means of securing them to each other. As such, the stopcock 19A allows for selective communication between the enclosure 17 and either one of pump 14 or 1.

9. A mini computer may be used to facilitate the use of these units mostly in the cases in which an electrical inflator is used. In such a case the mini computer will allow the functioning of the electrical pump to be controlled in routine measurements of the blood pressure. It will also allow the pump to work until the systolic or the upper pressure of the patient is reached and slightly exceeded. Then the computer will shut off the pump and allow the hand-held unit to be used for adjusting the pressure and for the continuation of the process. The computer also will allow certain functions to be used for control of devices such as D. Device. In such a case the computer will allow the unit to be inflated and the pressure to be held for a certain period of time, afterwards allowing a lower pressure to be applied and the course to continue. Importantly, this computer will also allow an alarm to be used if the pressure of the system drops unexpectedly or if there is a need for sudden inflation of the unit for a higher pressure as in an instance of bleeding; therefore, it will make a very useful unit. The hand-held unit will allow the pressure of this unit to be adjusted at any time that is required as it does occur with the use of D. Devices.

This computer part may be placed in the gauge area as shown at 13 FIG. 1.

10. The connection of the tubing and other pieces of these units may use methods which make such connections more secure. This may use springs or small connection securing pieces for such a secure connections.

It might be of interest to note that in the prototype original unit the applicant used foot pumps combined with hand-held bulb pumps for inflation and he was quite satisfied with their functioning.

What are the advantages of these units. These units have the advantages of being compact units that can be easily used by the user. Many models of these units give the advantage of "the human control" which so far has not been surpassed by computers. Some models will not use electricity and therefore can be used when electricity is not available. These units will also be cheaper than computer operated units. Also, in the case of the use with units such as D. Device these units will make the use of these devices much simpler and will also provide the chance of having the patient's blood pressure to be checked during the time of the use of this system for inflation of D. Device very conveniently. Computerized units will allow certain functions to be used for controlling special devices such as D. Device. In such a case, the computer will allow the unit to be inflated and the pressure to be held for a certain period of time, afterwards allowing a lower pressure to be applied and the course to continue. Importantly, this computer will also allow an alarm to be used if the pressure of the system drops unexpectedly or if there is a need for sudden inflation of the unit for a higher pressure as in the instance of bleeding; therefore, it will make a very useful unit. The hand-held unit will allow the pressure of this unit to be adjusted at any time that is required as it does occur with the use of D. Devices.

The applicant believes that these units will make the patient's care much easier and more productive and that is why he wishes to introduce this to the world community.

The exact size, relative sizes, the shape, the coloring and many other factors of these units may vary in different models.

I claim:

1. A device for setting the inflation pressure of an inflatable enclosure that applies pneumatic pressure to a living body and that has a port via which pressure fluid enters and exits the enclosure, comprising in combination with the enclosure:

pressurizing means that is not manually powered for inflating the enclosure;

pressurizing means that is manually powered for inflating the enclosure;

exhaust valve means for deflating the enclosure;

conduit means communicating with said pressurizing means that is not manually powered, said pressurizing means that is manually powered, said exhaust valve means, and said port of the enclosure;

wherein said pressurizing means that is manually powered and said exhaust valve means are disposed on a manually grippable body which comprises an inflation bulb that is manually squeezed to pressurize the enclosure and finger trigger means that operates said exhaust valve to deflate the enclosure; and in which said body comprises a guard wall that is disposed to a side of the inflation bulb so that both it and the bulb can be manually grasped and the bulb squeezed toward the wall.

2. A device as set forth in claim 1 in which said manually grippable body comprises a bent tube that is closed at one end by the bulb and that is connected at the other end to the conduit means.

3. A device as set forth in claim 2 in which said trigger means is disposed forwardly of said bulb relative to said wall.

4. A device as set forth in claim 3 in which said trigger means is pivotally mounted on said body.

5. A device as set forth in claim 1 further including a transportable stand on which said device is mounted.

6. A device as set forth in claim 5 in which said stand comprises a base and an upright extending from said base, and in which said pressurizing means that is not manually powered is disposed on said base.

7. A device as set forth in claim 6 in which said pressurizing means that is not manually powered comprises a foot operated pump disposed on said base.

8. A device as set forth in claim 6 in which said conduit means comprises a conduit extending upwardly along said upright from said pressurizing means that is not manually powered to a port of a stopcock valve means for connection to said enclosure having other ports to which said pressurizing means that is manually powered, said exhaust valve means, and said enclosure are coupled by other conduits of said conduit means.

9. A device as set forth in claim 8 including a pressure display mounted on said upright to sense pressure in said conduit means at a location between said pressurizing means that is manually not powered and said stopcock valve means.

10. A device as set forth in claim 6 in which said stand comprises at least one wheel providing for rolling along a horizontal surface, and said upright comprises a handle shaped to allow the stand to be vertically hanged.

11. A device as set forth in claim 10 including a basket disposed on said upright spaced from said base.

12. A device as set forth in claim 10 in which said base comprises a stop for frictionally engaging a horizontal surface when the stand is not being rolled to resist rolling.

13. A device as set forth in claim 6 in which said pressurizing means that is not manually powered comprises an electric-operated pump disposed on said base.

14. A device as set forth in claim 1 in which said inflatable enclosure comprises a blood pressure cuff.

15. A device for setting the inflation pressure of an inflatable enclosure that applies pneumatic pressure to a living body and that has a port via which pressure fluid enters and exits the enclosure, comprising in combination with the enclosure:

pressurizing means that is not manually powered for inflating the enclosure;

pressurizing means that is manually powered for inflating the enclosure;

exhaust valve means for deflating the enclosure;

conduit means communicating with said pressurizing means that is not manually powered, said pressurizing means that is manually powered, said exhaust valve means, and said port of the enclosure;

wherein stopcock valve means is disposed for establishing selective communication with said pressurizing means that is not manually powered and said pressurizing means that is manually powered with said enclosure via said conduit means.

16. A device as set forth in claim 15 in which a connection port is associated with said conduit means and said stopcock valve means to provide for connection of another inflatable device to said conduit means so as to enable such another inflatable device to be inflated by either one of said pressurizing means and deflated by said exhaust valve means.

17. A device as set forth in claim 15 in which said inflatable enclosure comprises a blood pressure cuff.

\* \* \* \* \*